United States Patent

Salari et al.

Patent Number: 5,219,845
Date of Patent: Jun. 15, 1993

[54] PHOSPHONATES AS ANTI-INFLAMMATION AGENTS

[75] Inventors: Hassan Salari, Ladner, Canada; Robert Bittman, Roslyn Heights, N.Y.

[73] Assignee: The University of British Columbia, Vancouver, Canada

[21] Appl. No.: 835,732

[22] Filed: Feb. 11, 1992

Related U.S. Application Data

[63] Continuation-in-part of Ser. No. 692,452, Apr. 25, 1991, abandoned.

[51] Int. Cl.$^5$ ............... A61K 31/685; A61K 31/66
[52] U.S. Cl. ............................ 514/77; 514/114; 514/129; 558/169; 558/186
[58] Field of Search ............... 558/169, 186; 514/77, 514/114, 129

[56] References Cited

U.S. PATENT DOCUMENTS 4,408,052 10/1983 Hozumi et al. ............... 546/22
4,515,722 5/1985 Yang et al. ............... 554/79

FOREIGN PATENT DOCUMENTS 1240534 1/1989 Canada .
0230575A2 4/1986 Fed. Rep. of Germany .

OTHER PUBLICATIONS

Chem. Abstr. 1985, 103(21), 178451f; Japan Kokai Tokkyo Koho 60-069088.

Primary Examiner—Mary C. Lee
Assistant Examiner—Michael G. Ambrose
Attorney, Agent, or Firm—Barrigar & Oyen

[57] ABSTRACT

The invention pertains to the synthesis and use as therapeutic agents of a group of substances with a glycerol backbone or aliphatic chain structure linked to a phosphorus atom and a polar head group. Depending on the polar head group, the substance has anti-cancer, anti-inflammatory, anti-allergy or anti-cardiovascular disease properties. Compounds of the formula:

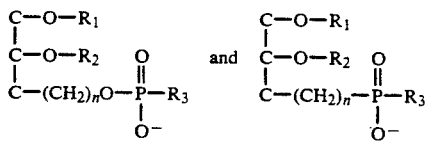

wherein n is 0 to 14 and $R_1$ is an alkyl group of $C_{12}$-$C_{20}$, $R_2$ is a methyl group, and wherein $R_3$ is an inositol analog head group, a $(CH_2)_m N^+(CH_3)_3$ group with m=2 to 10, a serine head group, or an ethanolamine head group, or of the formula

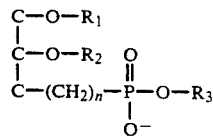

wherein $R_1$ and $R_2$ are as described above, n=0 or 1, and $R_3$ is $(CH_2)_m N^+(CH_3)_3$ (m=2-10) are claimed. This invention also pertains to the synthesis and use as therapeutic agents of a group of substances that have no glycerol backbone but have an aliphatic chain structure linked directly to a phosphorus atom of the general formula R—P(O)(O$^-$)OR' wherein R is a long-chain alkyl group such as hexadecyl or octadecyl and R' is a head group such as choline, glycerol, inositol, ethanolamine, or serine.

1 Claim, No Drawings

PHOSPHONATES AS ANTI-INFLAMMATION AGENTS

This application is a continuation-in-part of application Ser. No. 07/692,452; filed Apr. 25, 1991; abandoned.

FIELD OF THE INVENTION

This invention pertains to the synthesis and use as therapeutic agents of a group of substances with a glycerol backbone or aliphatic chain structure linked to phosphonocholine, phosphinocholine, phosphonoinositol, phosphinoinositol, or other phosphorus-containing head groups. Depending on the polar head group, the substance has anti-cancer, anti-inflammatory, anti-allergy, or anti-cardiovascular disease properties.

BACKGROUND OF THE INVENTION

West German Patent No. P 0230 575 A2, dated Apr. 12, 1986, discloses a group of glycerophospholipids compounds having an alkyl chain of C2-C22 and a methoxy group at the sn-2 position and a phosphocholine at the sn-3 position. These compounds are stated to be useful as anticancer agents.

U.S. Pat. No. 4,408,052, dated Feb. 25, 1981, assigned to Takeda Chemical Industries, Osaka, Japan, claims a group of phospholipid carbamates as useful as antitumor agents.

Canadian Patent No. 1,248,534, dated Jan. 10, 1989, granted to Takeda Chemical Industries of Japan, protects a group of ketolyso phospholipids, which purportedly are useful as antitumor agents.

U.S. Pat. No. 4,515,722, dated May 7, 1985, granted to Merck Sharp & Dohme, protects a group of phosphatidylinositol analogs which are evidently effective in inhibiting phospholipase C and thereby have utility as anti-inflammatory and analgestic agents.

None of these patents discloses a substance with a glycerol backbone linked to a phosphorus atom with a polar head group used as an anti-cancer, anti-inflammatory, anti-allergy, or anti-cardiovascular disease treating agents.

SUMMARY OF THE INVENTION

The present invention provides anti-leukemic phospholipids of the general formula:

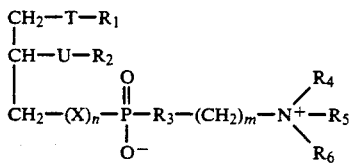

wherein T is an oxygen atom, U is an oxygen atom, or NH, $R_1$ is an aliphatic chain such as hexadecyl or octadecyl, $R_2$ is a methyl group when U is oxygen or when U is NH, X is a methylene group, n is 0 to 14, $R_3$ is either an oxygen atom or a methylene group, m is 2, 3, 4, 5, 6, 7, 8, or 9, and $R_4$, $R_5$ and $R_6$ represent alkyl groups containing 1 to 3 carbon atoms.

A compound of the formula:

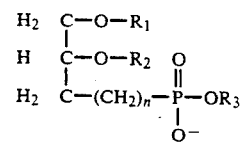

wherein n is 0 to 14 and $R_1$ is an alkyl group of $C_{12}$–$C_{20}$; wherein $R_2$ is a methyl group; and wherein $R_3$ is an inositol analog head group, a $(CH_2)_m N^+(CH_3)_3$ group with m=2 to 10, a serine head group, or an ethanolamine head group.

A phosphonate compound of the formula:

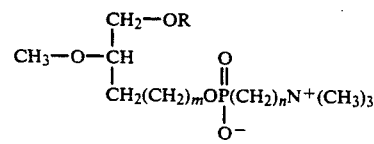

wherein R is an alkyl group such as hexadecyl or octadecyl, m=0 or 1, n=2-10, or the enantiomer thereof, or a mixture of stereoisomers.

Phosphonolipids of the general formula R—P(O)(O$^-$)OR' wherein R is an alkyl group such as hexadecyl or octadecyl and R' is a head group such as choline, glycerol, inositol, ethanolamine, or serine.

Phosphinates of the general formula:

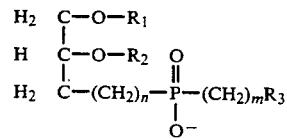

wherein n=0 or 1, $R_1$ and $R_2$ are as defined above and $R_3$ is an inositol or $N^+(R_4)_3$ group and m=2-10, and $R_4$ is an alkyl group such as methyl, ethyl, n-propyl, or isopropyl.

The phosphonate or phosphinate compounds as claimed in described include either of the opposite stereochemical configurations [(R) or (S)], or a mixture thereof.

A phosphinate for treatment of leukemic cells having the formula:

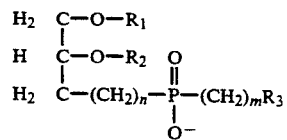

wherein $R_1$ is a long-chain alkyl group, $R_2$ is a methyl group, n=0 or 1, m=2 or 3, and $R_3$ is $N^+(CH_3)_3$, and pharmaceutically acceptable salts thereof, administered at a dosage of about 5 to 50 mg/l, with or without a carrier.

The compound as identified in the second paragraph of this summary can be used as an agent in inhibiting cancer cell growth when the compound is administered at a concentration in the range of 5 mg/l to 50 mg/l, and pharmaceutically acceptable acid or salts thereof; and a pharmaceutically acceptable carrier. This compound can also be used in the treatment of an inflammatory disease administered at 5–50 mg/l in a pharmaceutically acceptable carrier.

The compound as identified in the third paragraph of this summary can be used in the treatment of an inflammatory disease administered at 5–50 mg/l in a pharmaceutically acceptable carrier.

The compounds identified in the fourth paragraph of this summary can be used in the treatment of an inflammatory disease administered at 5–50 mg/l in a pharmaceutically acceptable carrier.

The phosphonates or phosphinates as identified in the second, third, fourth, fifth, and sixth paragraphs of this summary can be used in the treatment of allergic skin rashes, hayfever, and asthma or cardiovascular disease when administered to the patient at a dosage of about 5–50 mg/l in association with a pharmaceutically acceptable carrier.

A method of treating cancer, inflammation, allergy or cardiovascular disease in a mammal comprising treating the mammal with a therapeutic amount of a compound of the formula:

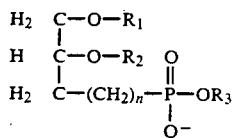

wherein n is 0 to 14 and $R_1$ is an alkyl group of $C_{12}$–$C_{20}$; wherein $R_2$ is a methyl group; and wherein $R_3$ is an inositol analog head group, a $(CH_2)_m N^+(CH_3)_3$ group with m=2 to 10, a serine head group, or an ethanolamine head group.

A method of treating cancer, inflammation, allergy or cardiovascular disease in a mammal comprising treating the mammal with a therapeutic amount of a compound of the formula:

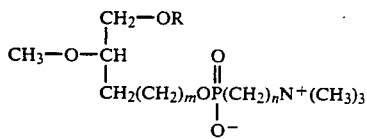

wherein R is an alkyl group such as hexadecyl or octadecyl, m=0 or 1, n=2–10, or the enantiomer thereof, or a mixture of stereoisomers.

A method of treating cancer, inflammation, allergy or cardiovascular disease in a mammal comprising treating the mammal with a therapeutic amount of a phosphonolipid of the general formula: R—P(O)(O⁻)(OR), wherein R is an alkyl group such as hexadecyl or octadecyl and R' is a head group such as chloline, glycerol, inositol, ethanolamine, or serine.

A method of treating cancer, inflammation, allergy or cardiovascular disease in a mammal comprising treating the mammal with a therapeutic amount of a phosphinate of the general formula:

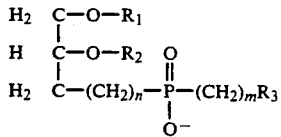

wherein n=0 or 1, $R_1$ and $R_2$ are as defined in claim 1, and $R_3$ is an inositol or $N^+(R_4)_3$ group and m=2–10, and $R_4$ is an alkyl group such as methyl, ethyl, n-propyl, or isopropyl.

The phosphonate or phosphinate compound can includes either of the opposite stereochemical configurations [(R) or (S)], or a mixture thereof.

A method of treating leukemic cells in a mammal comprising treating the mammal with a therapeutic amount of a phosphinate having the formula:

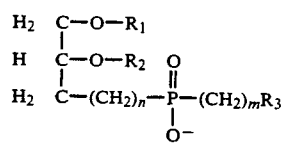

wherein $R_1$ is a long-chain alkyl group, $R_2$ is a methyl group, n=0 or 1, m=2 or 3, and $R_3$ is $N^+(CH_3)_3$, and pharmaceutically acceptable salts thereof, administered at a dosage of about 5 to 50 mg/l, with or without a carrier.

The present invention also provides phospholipids with the following structures:

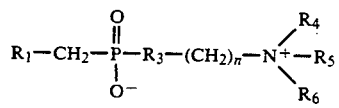

and

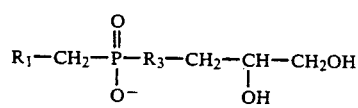

wherein $R_1$, $R_2$, $R_3$, $R_4$, $R_5$, $R_6$ and n are as defined above. The present invention provides phospholipids with an inositol group for use as anti-inflammatory agents:

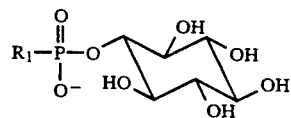

wherein $R_1$ is as defined herein above.

These phosphonates and phosphinates are useful as anti-cancer agents since they inhibit growth of leukemic and tumor cells, as anti-inflammatory and anti-allergic agents, and as anti-cardiovascular agents.

The invention also involves the use of one or several of the above-mentioned phosphonates and phosphinates for treatment of cardiovascular diseases, such as septic shock (cardiogenic shock, thrombosis and others) when given at 5–50 mg/l in a pharmaceutically acceptable acid or salt thereof, and carrier.

The invention is also directed to the use of phosphonates and phosphinates in the treatment of malignant cells, solid tumors of any type, leukemia and in bone marrow transplantation.

The invention also pertains to the use of phosphonates in the treatment of inflammatory diseases of any form, for example, arthritis, inflammatory bowel diseases, colitis, and pulmonary inflammation.

Further, the invention relates to the use of phosphonates in the treatment of allergic diseases of any form, such as asthma, allergic rhenitis, hay fever, skin rashes and seasonal allergies.

DETAILED DESCRIPTION OF SPECIFIC EMBODIMENTS OF THE INVENTION

Production of the Phospholipids of the Invention

(a) Synthesis of Phosphonocholines and Phosphonoglycerols

The phosphonocholines and phosphonoglycerols can be synthesized according to the following reaction sequence:

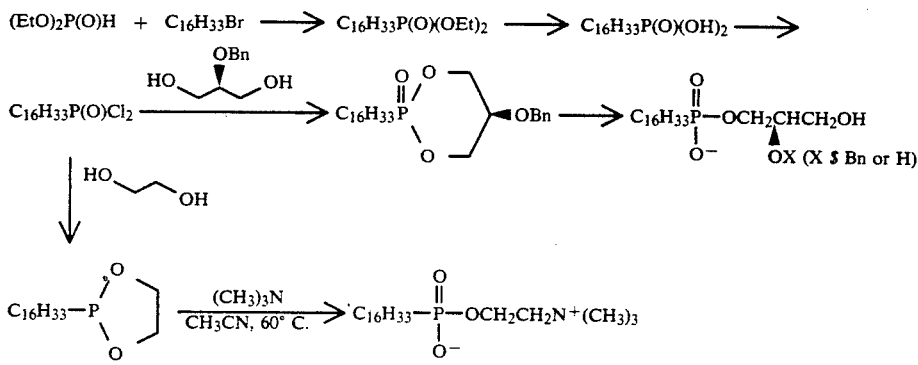

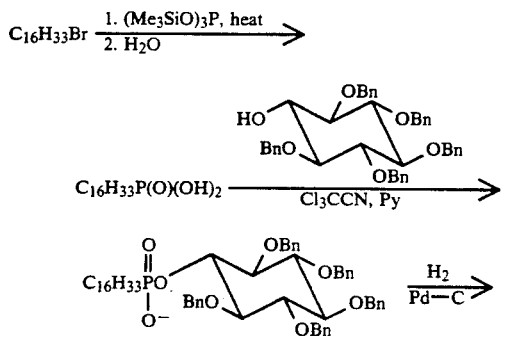

Diethyl phosphite is treated with hexadecyl (or octadecyl) bromide in a Michaelis-Becker reaction, giving the corresponding diethyl ester. The alkyl phosphonic acid is formed in situ from the ester, then treated with 2.1 equivalents of pyridine at 0° C. in tetrahydrofuran, followed by 2.1 equivalents of oxaloyl chloride at −78° C. under nitrogen. The phosphonic acid dichloride thus obtained is treated with either (R)-2-O-benzylglycerol (for conversion to phosphonoglycerol) or with ethylene glycerol to give the phospholane intermediate, which is reacted with triethylamine in acetonitrile at 75° C. in a pressure bottle to give phosphonocholine. The intermediates and products are purified by chromatography on silica gel G or by high-pressure liquid chromatography. The structures are established by nuclear magnetic resonance spectroscopy, mass spectrometry, and by elemental analysis.

(b) Synthesis of Phosphonoinositol

The phosphonoinositol is prepared by the following reaction sequence:

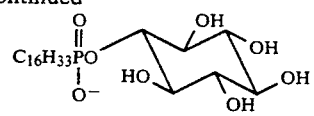

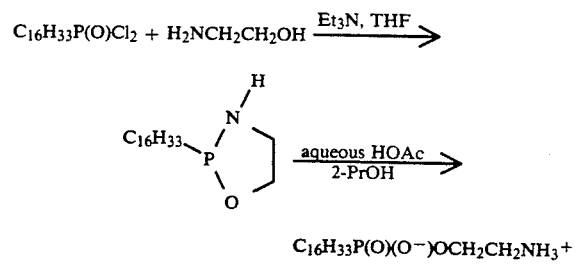

The phosphonoinositol is produced by reacting hexadecyl (or octadecyl) bromide with tris(trimethylsilyl)-phosphite under argon at 135° C. to form the alkyl phosphonic acid. After the excess phosphite is removed by distillation, the residue is purified and coupled to pentabenzylinositol in the presence of trichloroacetonitrile in pyridine at 60° C. to form pentabenzylinositol phosphonate. The coupling product is purified by chromatography on silica gel, the benzyl groups are removed by catalytic hydrogenolysis, and the product phosphonoinositol is purified by cation exchange and silica gel chromatography.

(c) Synthesis of Phosphonoethanolamine

The phosphonoethanolamine is prepared by the following reaction sequence:

$$C_{16}H_{33}P(O)Cl_2 + H_2NCH_2CH_2OH \xrightarrow{Et_3N, THF}$$

$$C_{16}H_{33}\underset{O}{\overset{H}{\underset{\diagdown}{\overset{\diagup}{P}}}}\!\!\Big] \xrightarrow[\text{2-PrOH}]{\text{aqueous HOAc}}$$

$$C_{16}H_{33}P(O)(O^-)OCH_2CH_2NH_3{}^+$$

To a solution of the alkyl phosphonic acid dichloride and triethylamine in tetrahydrofuran is added a solution of 2-aminoethanol in tetrahydrofuran. Evaporation of the solvent under reduced pressure gives the intermediate phospholane, which is purified by column chromatography, dissolved in 2-propanol, and then hydrolyzed by using a mixture of glacial acetic acid in water (1:4 by volume).

(d) Synthesis of Phosphonoserine

The phosphonoserine is prepared by the following reaction

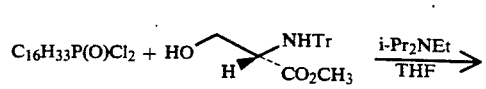

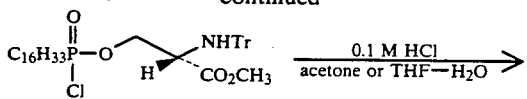
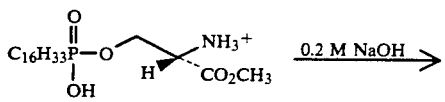
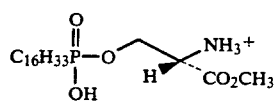

To a solution of the alkyl phosphonic acid dichloride in tetrahydrofuran and diisopropylethylamine in tetrahydrofuran is added a solution of N-tritylserine methyl ester in tetrahydrofuran. The intermediate N-tritylserine methyl ester is purified by silica gel chromatography, then subjected to detritylation with 0.1M hydrochloric acid and alkaline hydrolysis of the methyl ester. The product is purified by Dowex 50W-X8 (H+ form) followed by silica gel chromatography.

(e) Production of Glycerol-Linked Phosphonolipids

Phosphonocholines are prepared by the following reaction sequence:

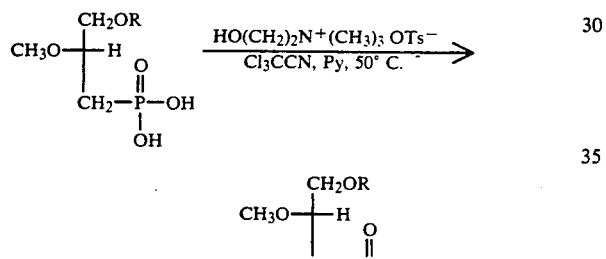

(R = $C_{16}H_{33}$ or $C_{18}H_{37}$)

The rac-phosphonic acid shown above is prepared by proceeding according to the following sequence of reactions. First, a n-alkyl allyl ether is reacted with methanol in the presence of zinc oxide and iodine; alkyl groups other than methyl can be conveniently introduced by this method (reference: Rosenthal, A. F.; Kosolapoff, G. M.; Geyer, R. P. *Recl. Trav. Chim. Pays-Bas* 1964, 83, 1273). The 1-O-alkyl-2-O-methyliodopropane is treated with triethyl phosphite, affording the corresponding diethyl phosphonate ester, which is hydrolyzed to give the phosphonic acid. Phosphonocholine is obtained by reaction with dry choline tosylate (9 equivalents) in the presence of trichloroacetonitrile in pyridine at 50° C. for 2 days.

The corresponding glycerol-linked phosphonoethanolamine is prepared by reaction of the phosphonic acid with N-(tert-butoxycarbonyl)-ethanolamine (N-t-Boc-ethanolamine) in the presence of trichloroacetonitrile or 1H-tetrazole; after purification of the coupling product by silica gel chromatography, the Boc protecting group is removed under standard conditions (50% trifluoroacetic acid in dichloromethane at 0° C.).

The corresponding glycerol-linked phosphonoserine is prepared in a similar fashion, using N-tritylserine methyl ester for coupling with the phosphonic acid.

The acid-labile trityl group is removed by treatment with 0.1M hydrochloric acid in tetrahydrofuran-water (1:1), and then the methyl ester is hydrolyzed by using 0.2M sodium hydroxide. Purification is by silica gel chromatography.

(f) Production of Glycerol-Linked Isosteric Phosphonates

Isosteric phosphonates are prepared according to the following reaction sequences:

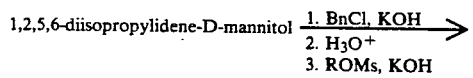

(R = hexadecyl or octadecyl)

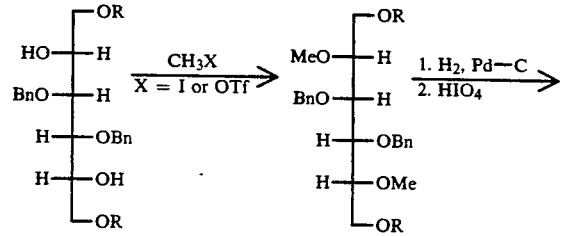

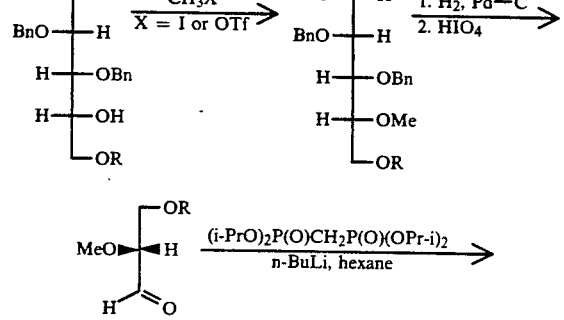

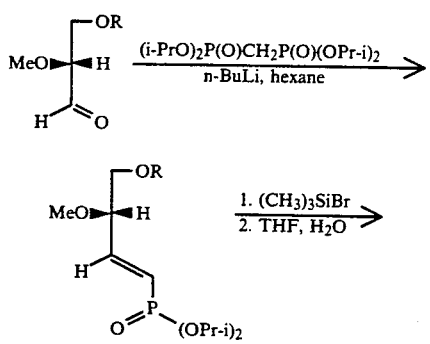

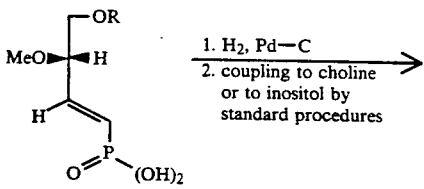

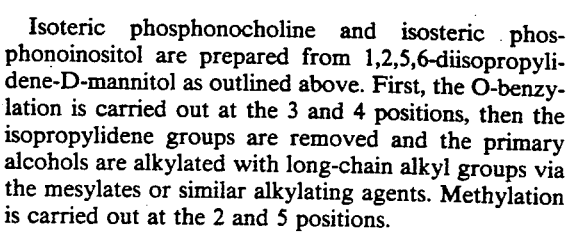

Isoteric phosphonocholine and isosteric phosphonoinositol are prepared from 1,2,5,6-diisopropylidene-D-mannitol as outlined above. First, the O-benzylation is carried out at the 3 and 4 positions, then the isopropylidene groups are removed and the primary alcohols are alkylated with long-chain alkyl groups via the mesylates or similar alkylating agents. Methylation is carried out at the 2 and 5 positions.

After catalytic hydrogenolysis, periodic acid cleavage gives the aldehyde. Reaction of the aldehyde with tetraisopropyl methylenebisphosphonate and n-butyllithium in hexane at 0° C. gives the phosphonic ester, which is hydrolyzed to the corresponding phosphonic acid by using trimethylsilyl bromide followed by aqueous workup. The vinyl group is reduced, and the phosphonic acid is coupled to choline tosylate to give the desired phosphonocholine compound or to suitably protected inositol, followed by deprotection, to give the desired phosphonoinositol compound. The products are purified by ion-exchange chromatography followed by silica gel chromatography. Phosphonoglycerols are available by a similar route.

An alternative procedure for making phosphonoinositols and phosphonocholines is illustrated below.

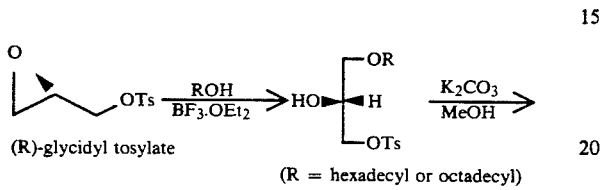

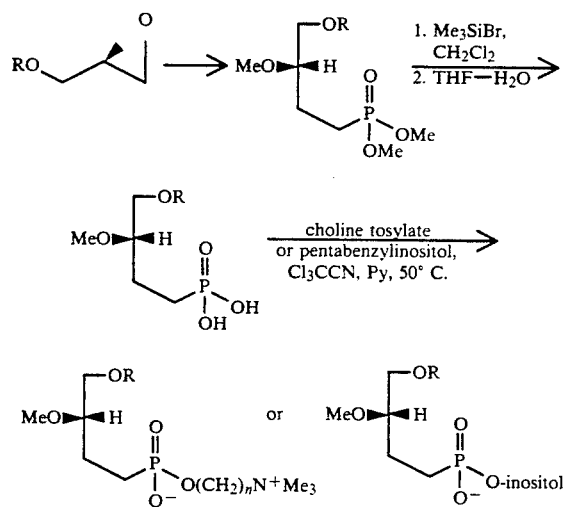

The above reaction sequence shows the use of (R)-O-hexadecyl or -octadecyl glycidol as the starting material. Use of (S)-hexadecyl or octadecyl glycidol gives the enantiomeric phosphonolipid.

(g) Production of Glycerol-Linked Phosphinocholines

The nonisosteric phosphinocholines are prepared according to the following reaction sequence:

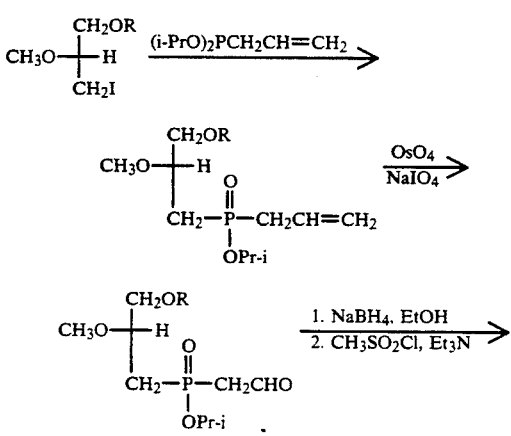

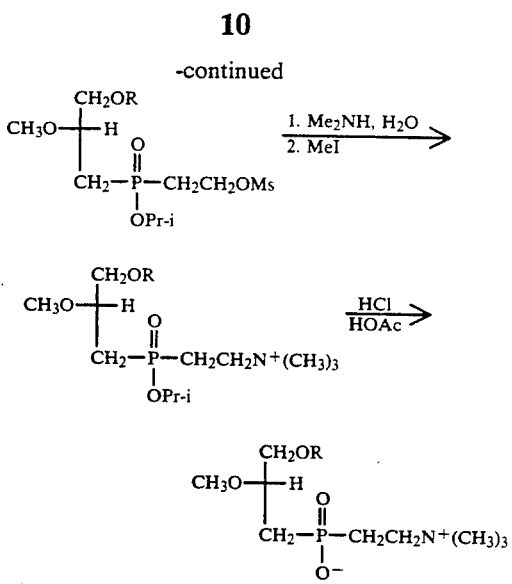

Reaction of diisopropylallylphosphinate with 1-O-alkyl-2-O-methyliodopropane gives isopropyl 2-methoxy-3-O-alkylpropyl(allyl)phosphinate, which is cleaved with osmate-periodate, and reduced with sodium borohydride in ethanol to the hydroxyethylphosphinate. The latter is converted to the mesylate and allowed to react with aqueous dimethylamine, followed by quaternization to give the phosphinate compound.

(h) Production of Glycerol-Linked Isosteric Phosphinates

Isosteric phosphinocholines and phosphinoinositols are prepared according to the following reaction sequences:

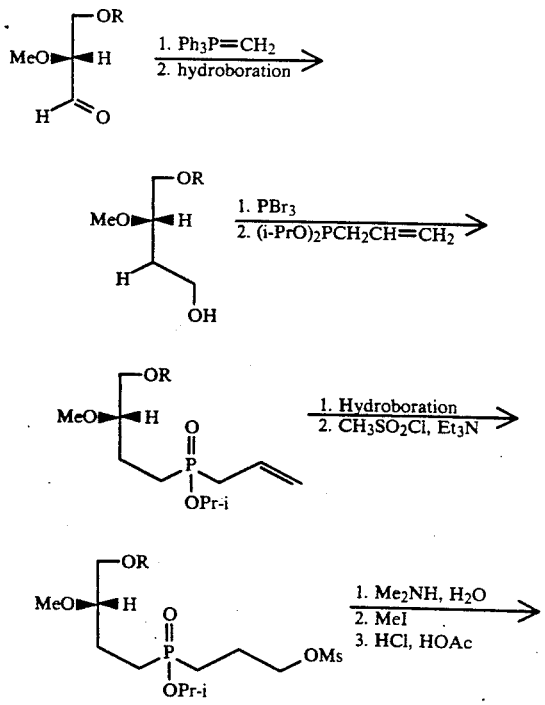

-continued

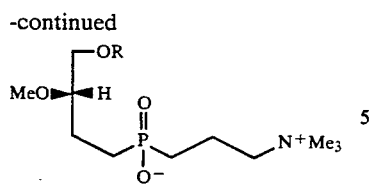

Isosteric phosphinocholine is prepared as outlined by the reaction sequence shown above. Wittig reaction of the aldehyde followed by hydroboration gives the alcohol, which is then converted into the desired phosphinate. Hydroboration gives an alcohol (not shown) that can be coupled to a protected inositol to yield the corresponding phosphinoinositol. Mesylation of the alcohol gives the phosphinate compound, which is aminated, then treated with methyl iodide, and the phosphonate ester is hydrolyzed to give the isosteric phosphinocholine.

(i) Production of Agents with Modified Distances between the Phosphorus and Nitrogen Atoms The distance between the phosphorus and nitrogen atoms in the phosphonolipids is varied by using procedures known in the corresponding phosphate-containing compounds (references: Ali, S.; Bittman, R. *Chem. Phys. Lipids* 1989, 50, 11–21; Isaacson, Y. A.; Deroo, P. W.; Rosenthal, A. F.; Bittman, R.; McIntyre, J. O.; Bock, H-G.; Gazzotti, P.; Fleischer, S. *J. Biol. Chem.* 1979, 254, 117–126; Ukawa, K.; Imamiya, E.; Yamamoto, H., et al. *Chem. Pharm. Bull.* 1989, 37, 1249–1255). One method for conversion of the glycerol derivative to the phosphonocholine analog with a variable number of methylene groups between the phosphorus and nitrogen atoms is shown below.

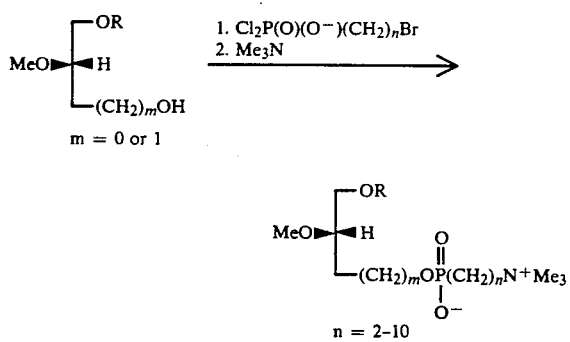

m = 0 or 1 n = 2–10

BIOLOGICAL ACTIVITY

1. Anti-Cancer Activity

Several laboratory tests have been conducted to establish that phosphonates kill cancer cells.

It has been discovered that a phosphonate of the following structure:

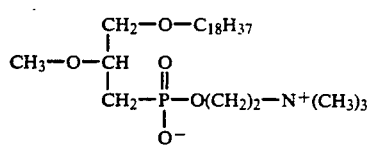

inhibits thymidine incorporation into DNA of several cancer cell lines. This behavior is indicative of anti-cancer activity.

EXAMPLE 1

Experiments were performed with three different cell lines: (1) with a mouse myelomonocytic leukemic cell line (WEHI-3B cells), (2) a human myeloleukemic cell line (HL-60) and a human cervical tumor cell line (C-41)). Cells were cultured in RPMI-1640 medium supplemented with 10% fetal bovine serum, mercaptoethanol (5 $\mu$g/ml), penicillin (50 units/ml), streptomycin (50 $\mu$g/ml), in an atmosphere of 5% $CO_2$. The cells were passaged weekly by serial 1/10 to 1/10000 dilutions. The cell viability and growth were constantly monitored by staining with trypan blue exclusion dye or the incorporation of tritiated thymidine.

$^3$H-Thymidine incorporation

Cells were placed in 96-well plates at $2\times10^4$ cells/well in 200 $\mu$l of medium and another 5 $\mu$l of medium containing the drugs was added. Control cultures were incubated without drugs. Cells in 96-well plates were incubated in a $CO_2$ incubator for 24 hours. The cells were then pulsed with 0.1 $\mu$Ci of [$^3$H]thymidine for 24 hours prior to the harvesting. The cells were harvested using a Brandel cell harvester model M-12, and collected on Whatman glass microfilters. The radioactivity associated with the filters was counted in a liquid scintillation counter and plotted as percent survival versus concentration of phosphonate, and the data were compared with [$^3$H]thymidine incorporation into the untreated cells.

Table I shows the effect of various concentrations of the phosphonate of the following formula on the growth of WEHI-3B cells:

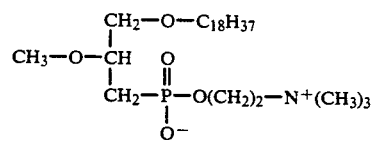

TABLE I

| Thymidine uptake during 24 hours | |
|---|---|
| phosphonate concentration ($\mu$M) | thymidine uptake (% of control) mean ± s.d. |
| 0 | 100 |
| 0.62 | 137 ± 6 |
| 1.25 | 93 ± 7 |
| 2.5 | 91 ± 4 |
| 5 | 88 ± 11 |
| 10 | 76 ± 6 |
| 20 | 48 ± 4 |
| 40 | 43 ± 15 |

Table II shows results of thymidine uptake by WEHI-3B and HL-60 cells during 48 hours of incubation.

TABLE II

| Thymidine uptake during 48 hours | | |
|---|---|---|
| | thymidine uptake (% of control) | |
| phosphonate concentration ($\mu$M) | WEHI-3B cells | HL-60 cells |
| | Mean ± s.d. n = 8 | |
| 0 | 100 | 100 |
| 0.62 | 93 ± 6 | 84 ± 5 |
| 1.25 | 90 ± 5 | 76 ± 4 |
| 2.5 | 86 ± 8 | 63 ± 4 |

TABLE II-continued

Thymidine uptake during 48 hours

| phosphate concentration (μM) | thymidine uptake (% of control) | |
|---|---|---|
| | WEHI-3B cells | HL-60 cells |
| | Mean ± s.d. n = 8 | |
| 5 | 61 ± 6 | 24 ± 3 |
| 10 | 23 ± 2 | 3 ± 2 |
| 20 | 18 ± 8 | 1 ± 0 |

Table III shows the results of thymidine uptake by WEHI-3B and HL-60 cells during 72 hours of incubation.

TABLE III

Thymidine uptake during 72 hours

| phosphonate concentration (μM) | thymidine uptake (% of control) | |
|---|---|---|
| | WEHI-3B | HL-60 |
| | Mean ± s.d., n = 8 | |
| 0 | 100 | 100 |
| 0.62 | 85 ± 3 | 93 ± 4 |
| 1.25 | 86 ± 4 | 81 ± 4 |
| 2.5 | 82 ± 6 | 66 ± 3 |
| 5 | 60 ± 4 | 16 ± 4 |
| 10 | 26 ± 3 | 5 ± 1 |
| 20 | 10 ± 3 | 1 ± 0.9 |
| 40 | 7 ± 3 | 3 ± 1 |

Effect of phosphonate of the following structure on thymidine incorporation into DNA of WEHI-3B cells.

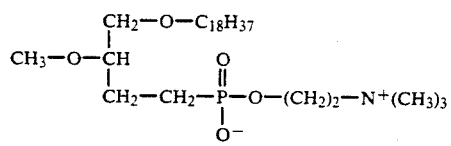

TABLE IV

Thymidine uptake after various days (% of control)

| phosphonate concentration (μM) | day 1 | day 2 | day 3 |
|---|---|---|---|
| | Mean, n = 5 | | |
| 0 | 100 | 100 | 100 |
| 1.25 | 94 | 84 | 77 |
| 2.5 | 72 | 67 | 54 |
| 5 | 34 | 22 | 12 |
| 10 | 18 | 13 | 10 |
| 20 | 8 | 2 | 1 |
| 40 | 3 | 2 | 2 |

Table V demonstrates the effect of phosphonate of the above structure on the incorporation of thymidine into DNA of the C-41 cell line (a human cervical tumor cell)

TABLE V

Thymidine uptake into DNA of C-41 cell line

| phosphonate concentration (μM) | thymidine uptake (% of control) Mean, n = 3 |
|---|---|
| 0 | 100 |
| 2.5 | 88 |
| 5 | 63 |
| 10 | 42 |
| 20 | 41 |
| 40 | 16 |

Table VI shows the effect of the above phosphonate on tumor growth in mice. BALB/C mice were injected with 3-Lewis lung carcinoma under the skin at the back. Three days after injection of tumor cells the treatment was initiated with 50 mg/day orally once a day. In the control group the mice received only the carrier mucilage of tragacanth. As seen in Table VI, in control animals the first sign of a detectable tumor was observed after the seventh day of post cell injection. In the phosphonate-treated animals, the tumor growth was retarded by approximately 6 days. The tumor size in the phosphonate-treated animals remained below that in the control animals throughout the experiments.

TABLE VI

| Days after tumor implant | Tumor volume (mm³) | |
|---|---|---|
| | control | +phosphonate |
| 0 | 0 | 0 |
| 7 | 30 | 0 |
| 10 | 120 | 0 |
| 17 | 250 | 100 |
| 18 | 432 | 175 |
| 20 | 670 | 252 |
| 22 | 810 | 500 |

2. Anti-Inflammatory Activity

Example 1

Effect of the phosphonate of the following formula on the activation of human neutrophils

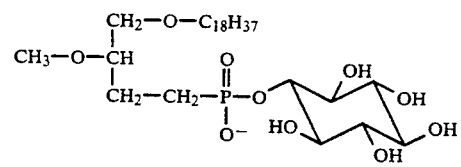

Superoxide anion generation in neutrophils has been used as an index of cell activation. The continuous spectrophotometric measurement of a superoxide dismutase inhibitable reduction of ferricytochrome C at 549 nm was used to demonstrate superoxide anion generation. Human neutrophils were stimulated with 1 μM FMLP (N-formylmethionyl-leucyl-phenylalanine). A rapid generation of superoxide was observed. Table VII shows the inhibition of superoxide anion generation by 10 μM phosphonate after various times.

TABLE VII

| Time (min) | absorbance at 549 nm | | |
|---|---|---|---|
| | control | FMLP | FMLP + phosphonate |
| 0 | 0 | 0 | 0 |
| 1 | 0.001 | 0.1 | 0.03 |
| 2 | 0.002 | 0.14 | 0.04 |
| 3 | 0.01 | 0.16 | 0.04 |
| 4 | 0.015 | 0.16 | 0.04 |

Example 2

Effect of phosphonate on neutrophil degranulation and lysosomal enzyme release (elastase)

Petri dishes were coated with [³H]elastin and were used to assess the release of elastase. Neutrophils (10⁶) in 500 μl of medium were added to each Petri dish well. Addition of 1 μM FMLP for 1 hour at 37° C. stimulated elastase release as determined by the breakdown of elastin. Phosphonate inhibited the neutrophil degranulation and the release of elastase (Table VIII).

TABLE VIII

| phosphonate concentration (μM) | μg elastin degraded/$10^6$ cells/hr Mean, n = 3 |
|---|---|
| 0 | 17 |
| 2.5 | 16 |
| 5 | 8 |
| 10 | 6 |
| 25 | 4 |
| 50 | 3 |

3. Anti-Arthritis Activity of Phosphonates

In the synovial fluids of patients with arthritis there is an accumulation of two types of crystals, calcium pyrophosphate dihydrate (CPPD) and monosodium urate (MSU). These two crystals types are the major contributors to the development of arthritis by causing rapid leukocyte activation. Table IX shows that phosphonates (50 μM) inhibited leukocyte activation in response to CPPD. Table X shows the inhibition in response to MSU.

TABLE IX

| Time (min) phosphonate | chemiluminescence (mV) | |
|---|---|---|
| | CPPD | CPPD+ |
| 0 | 0 | 0 |
| 1 | 25 | 0 |
| 2 | 175 | 0 |
| 3 | 500 | 100 |
| 4 | 750 | 275 |
| 5 | 900 | 300 |
| 6 | 800 | 250 |
| 7 | 500 | 150 |

TABLE X

| Time (min) phosphonate | chemiluminescence (mV) | |
|---|---|---|
| | MSU | MSU+ |
| 0 | 0 | 0 |
| 1 | 200 | 10 |
| 2 | 500 | 50 |
| 3 | 600 | 75 |
| 4 | 675 | 80 |
| 5 | 550 | 50 |
| 6 | 400 | 20 |

4. Anti-Allergic Activity of Phosphonates

Asthma is an allergic disease caused by the contraction of airway smooth muscles in response to activation with contractile agonists such as leukotriene $D_4$ ($LTD_4$). As seen in Table XI, phosphonates at 5 μM inhibited $LTD_4$-induced contraction of trachea from guinea pigs.

TABLE XI

| $LTD_4$ dose (μM) | contraction (% of max carbachol) | |
|---|---|---|
| | no phosphonate | with phosphonate |
| 0 | 0 | 0 |
| 0.01 | 7 | 0 |
| 0.1 | 21 | 0 |
| 1 | 45 | 0 |
| 10 | 50 | 8 |

Inhibition of tracheal smooth muscle contraction by phosphonates supports the anti-allergic and asthmatic properties of these agents.

5. Anti-Thrombolytic and Cardiovascular Activity

Thrombosis is the result of activation of platelets by agents such as platelet activating factor (PAF). Platelet activation is associated with aggregation and release of vasoactive compounds such as serotonin that have profound effects on heart and vascular tissues.

The effects of phosphonate on aggregation of platelets caused by PAF or thrombin are shown in Table XII. As seen in Table XII, PAF at 1 μM or thrombin at 1 unit/ml caused 60-70% aggregation of platelets. In the presence of various concentrations of phosphonate a dose-dependent inhibition of platelet aggregation is obtained. At 10 μM of phosphonate, a complete inhibition of platelet aggregation is seen.

TABLE XII

| phosphonate dose (μM) | platelet aggregation (% of control) | |
|---|---|---|
| | thrombin (1 unit) | PAF (1 μM) |
| 0 | 100 | 100 |
| 0.5 | 58 | 74 |
| 1 | 29 | 48 |
| 5 | 7.5 | 26 |
| 10 | 0 | 0 |

Phosphonates also inhibited serotonin release from platelets activated with thrombin or PAF. As seen in Table XIII, phosphonate at 10 μM blocked serotonin release entirely.

TABLE XIII

| phosphonate dose (μM) | serotonin release (% of control) | |
|---|---|---|
| | thrombin (1 unit) | PAF (1 μM) |
| 0 | 100 | 100 |
| 1 | 76 | 80 |
| 5 | 36 | 48 |
| 10 | 16 | 28 |

The data in Table XIII support the anti-cardiovascular disease activity of phosphonates.

6. Anti-Hypotensive Activity

Administration of PAF intravenously causes severe hypotension. Phosphonates were shown to block PAF-induced hypotension in rats. When given at 5 mg/kg, phosphonates inhibited the hypotensive activity of PAF dramatically. As seen in Table XIV, normal rat blood pressure was about 150 mm Hg, and this dropped to about 40 mm Hg after administration of PAF (10 μg/kg). Animals given phosphonates (5 mg/kg) had only slightly reduced blood pressure after the injection of PAF, suggesting that phosphonates are anti-hypotensive agents.

TABLE XIV

| PAF dose (μg/kg) | blood pressure (mm Hg) | |
|---|---|---|
| | no phosphonate | with phosphonate |
| 0 | 150 | 148 |
| 0.5 | 135 | 145 |
| 1 | 120 | 145 |
| 2.5 | 100 | 140 |
| 5 | 60 | 140 |
| 10 | 40 | 130 |

These data strongly support the anti-hypotensive and cardiovascular activity of phosphonates.

Usage and Dosage

An effective concentration of phosphonate (normally 5-50 mg/l) can be given orally, intravenously (i.v.), intramuscularly (i.m.) or subcutaneously (s.c.), in the form of tablets (orally), capsules (orally), or injection ampules (i.v., i.m., s.c.). The drug can be applied in the form of a rubbing cream. Tablets can be prepared via compression of 50 mg of phosphonates, 200 mg of lactose, and 50 mg Avicel(TM). Capsules are made by making bilayers of liposomal phosphonates in the concentrations of 5-50 mg with lecithin. Injection solutions are made either in water or propylene glycol with an upwardly adjusted pH in phosphate buffer. The drug solution is sterilized through a filter of 0.22 mm. Solutions can be made in 20% propylene glycol with about 0.5% of a preservative such as ascorbic acid.

As will be apparent to those skilled in the art in the light of the foregoing disclosure, many alterations and modifications are possible in the practice of this invention without departing from the spirit or scope thereof.

What is claim is:

1. A method of treating inflammation in a mammal afflicted with inflammation comprising treating the mammal with a compound of the formula:

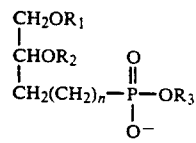

wherein n is 0 to 14; wherein $R_1$ is an alkyl group of $C_{12-20}$; wherein $R_2$ is a methyl group; and wherein $R_3$ is an inositol analog head group, a $(CH_2)_m N^+(CH_3)_3$ group wherein m is 2 to 10, a serine head group, or an ethanolamine head group, the compound being administered at a concentration in the range of 5-50 mg/1 in a pharmaceutically acceptable carrier.

* * * * *

UNITED STATES PATENT AND TRADEMARK OFFICE
CERTIFICATE OF CORRECTION

PATENT NO. : 5,219,845

DATED : June 15, 1993

INVENTOR(S) : Hassan Salari and Robert Bittman

It is certified that error appears in the above-identified patent and that said Letters Patent is hereby corrected as shown below:

Column 4, line 36, delete "$R_3$".

Column 4, line 40, following "above.", insert --$R_3$ is an oxygen or methylene group.--.

Column 5, line 27, change: [structure with $C_{16}H_{33}$-P bonded to O, O] to: [corrected structure with $C_{16}H_{33}$-P(=O) bonded to O, O].

Column 5, line 42, change "glycerol" to --glycol--.

Column 6, line 46, change: [structure with $C_{16}H_{33}$-P bonded to N-H, O] to: [corrected structure with $C_{16}H_{33}$-P(=O) bonded to N, O].

Column 8, line 58, change "Isoteric" to --Isosteric--.

Column 11, line 40, change "$Cl_2P(O)(O^-)(CH_2)_nBr$" to --$Cl_2P(O)(CH_2)_nBr$--.

UNITED STATES PATENT AND TRADEMARK OFFICE
CERTIFICATE OF CORRECTION

PATENT NO. : 5,219,845
DATED : June 15, 1993
INVENTOR(S) : Hassan Salari and Robert Bittman It is certified that error appears in the above-identified patent and that said Letters Patent is hereby corrected as shown below:

Column 15, line 24, following "CPPD+" add —Phosphonate—.

Column 15, line 37, following "MSU+" add —Phosphonate—.

Column 17, line 10, change "mm" to —$\mu$m—.

Column 17, line 19, change "claim" to —claimed—.

Signed and Sealed this

Seventeenth Day of May, 1994

Attest:

BRUCE LEHMAN

Attesting Officer        Commissioner of Patents and Trademarks